(12) United States Patent
Heffron

(10) Patent No.: US 6,215,008 B1
(45) Date of Patent: Apr. 10, 2001

(54) FLUORESCENT DYES

(75) Inventor: Peter J. Heffron, Flemington, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/454,194

(22) Filed: Dec. 3, 1999

(51) Int. Cl.$^7$ .......................... C09B 3/22; C07C 211/00; C07C 43/02; C07C 22/00
(52) U.S. Cl. .......................... 552/276; 552/276; 552/277; 552/279; 552/280; 552/281; 564/426; 568/632; 568/634; 570/183
(58) Field of Search ........................ 552/276, 279, 552/277, 280, 281; 570/183; 568/632, 634; 564/426

(56) References Cited

U.S. PATENT DOCUMENTS

| 4,486,587 | 12/1984 | Seybold | 455/99 |
| 5,958,780 | 9/1999 | Asher et al. | 463/56 |

OTHER PUBLICATIONS

Nair et al. (DN 76:73710 CAPLUS; abstract of Indian J. Chem. (1971), 9(9), 925–7.*

* cited by examiner

*Primary Examiner*—Sabiha N. Qazi
(74) *Attorney, Agent, or Firm*—Kenneth Crimaldi

(57) ABSTRACT

Fluorescent dyes which fluoresce a variety of colors are prepared from substituted isoviolanthrone and substituted isoviolanthrone by reductive alkylation with alkyl halides in the presence of zinc.

2 Claims, No Drawings

FLUORESCENT DYES

The present invention is directed to fluorescent dyes useful for leak detection, pipeline interface detection, and crude oil detection in depleted wells. The invention provides fluorescent dyes which fluoresce at a variety of wavelengths.

BACKGROUND OF THE INVENTION

Fluorescent dyes have been produced from violanthrone (C.I. Vat Blue 20) and isoviolanthrone (C.I. Vat Violet 10), nine-ring aromatic diketone structures, by reductive alkylation with alkyl halides and zinc powder at elevated temperatures. These dyes fluoresce a green-yellow color. Complex apparatus may have a number of fluid lines; thus, it would be desirable to be able to differentiate by fluorescent dye color the source of a leak.

Also, the dyes may be used for tagging and identifying liquids, such as petroleum fuels. The availability of fluorescent dyes of a variety of hues increases the utility of such dyes for this purpose. Fluorescent dyes may be detected by apparatus described in U.S. Pat. No. 5,958,780, the teachings of which are incorporated herein by reference. Two fluorescent dyes which fluoresce at significantly different wavelength may be used in a binary tagging system which provides for an essentially unlimited number of identifying combinations.

Accordingly, it is a general object of the present invention to provide fluorescent dyes which fluoresce at wavelengths different from currently available fluorescent dyes.

SUMMARY OF THE INVENTION

In accordance with the present invention, fluorescent dyes which fluoresce at a variety of wavelengths are produced by reductive alkylation of substituted violanthrone and substituted isoviolanthrone. The substituted violanthrone and substituted isoviolanthrone structures are reacted with alkyl halides and zinc, the reductive alkylation removing the dione functionality from the structure and adding between 2 and 6 alkyl groups, on average, to the ring structures. Depending upon the number of substituent groups on the ring structure, and the number and structure of the alkyl groups added, fluorescent dyes which fluoresce at a variety of wavelength are produced. Example of fluorescent colors which are produced include green, green-yellow, yellow and orange.

DETAILED DESCRIPTION OF CERTAIN PREFERRED EMBODIMENTS

Substituted voilanthrones used as starting materials in accordance with the invention have the general formula:

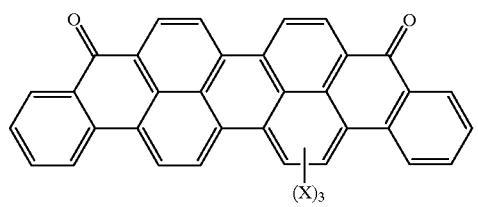

(I)

where the Xs are the same or different and are selected from Cl, H, F, I, O—(C1–C8)alkyl, and $NY_2$ where the Ys are the same or different and are selected from H or (C1–C8)alkyl; provided that at least one X is other than H.

Substituted isoviolanthrones used as starting materials have the general formula, where the Xs as defined above:

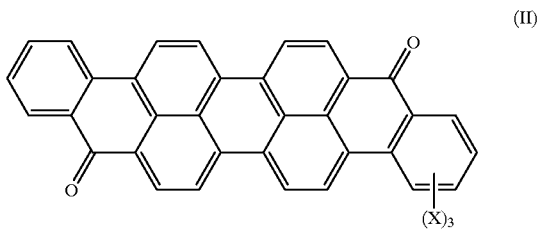

(II)

where the Xs are as defined above; again providing that at least one X is not H. Because it is known that substituent groups tend to de-stabilize multi-ring structures of this type, it is surprising that the substituted violanthrone and substituted isoviolanthrone structures may be alkylated by the relatively harsh conditions of reductive alkylation without break-down of the ring structure.

In the above formulae (I) and (II), the slash lines into the ring structures indicate that the Xs may be on any available location on the nine-ring structures.

Examples of suitable starting dyes include for example:

C.I. Vat Blue 18

C.I. Vat Violet 1

C.I. Vat Violet 9

C.I. Vat Black 16

C.I. Vat Green 1.

The starting dyes are reacted with an excess alkyl halide, generally an alkyl chloride, in the presence of zinc so as to provide a high degree of alkylation of the ring structure. Reductive alkylation occurs at the ketone group sites and additional alkylation occurs around the ring structures when an excess of alkyl halide is used. Typically, on each molecule, the ring structure is alkylated with 2–6 alkyl groups, most typically 6 alkyl groups, when a substantial excess of alkyl halide is used as the reactant. By "excess" is meant herein an amount above 6 moles of alkyl halide per mole of dye of formula (I) or (II).

The alkyl groups of the alkyl halides have between 1 and 12 carbon atoms, preferably between 6 and 12. Preferably the alkyl groups of the alkyl halides are linear. As the zinc is provided in powdered, zero valence, form, it is generally used at a considerable stoichiometric excess. In the reaction, both reductive and non-reductive alkylation occur. In substituted ring structures, some loss of substituent (X) groups may occur, though it is difficult to determine the extent, if any, this may occur.

Accordingly, the Dyes in accordance with the invention have the general formulae:

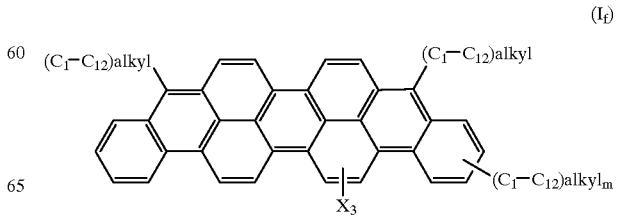

($I_f$)

-continued

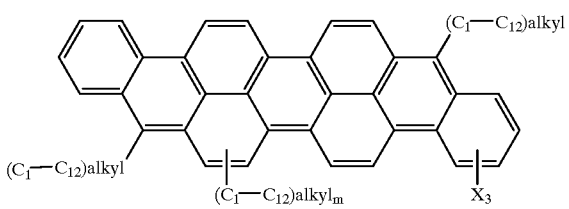

(II_f)

where the Xs are as defined above; at least one X is other than H; and m=0–4.

The dyes produced in accordance with the invention are liquids, making them easy to mix with other fluids, such as petroleum fuels and air conditioning refrigerants. The dyes are fully miscible with both petroleum fuels and refrigerants.

The invention will now be described in greater detail by way of specific examples:

EXAMPLE 1

Into a 1 liter three necked flask fitted with thermometer and Dean Stark trap with condenser was charged 440 grams (2.16 g—mol) lauryl chloride. This was followed by the addition of 52.3 grams (0.10 g—mol) C.I. Vat Violet 1. The assembly was wrapped in insulation gauze.

The stirred mixture was dried under slight vacuum by heating to 150° C. to remove moisture. The flask was purged with a nitrogen atmosphere. The temperature was then raised to 205–210° C. and a charge (3.0 g.) of zinc powder was quickly added through the third neck, and fitted with a stopper. The temperature was raised further to 210–215° C. wherein a second charge (3.0 g) of zinc powder was quickly made. The temperature was raised further to 223–225° C. and held in this temperature range for 1 hour.

As the reaction initiated and proceeded, the internal temperature of the contents was lowered by the formation of product(s). Six additional charges of zinc powder (3.0g) were added over a period of two hours at twenty-minute intervals. During this time hydrochloric acid was formed. The temperature was slowly raised to 223–225° C. and held there for eight hours. Then the temperature was raised to 238–240° C. for four hours to complete the reaction.

The temperature was then lowered to 80° C. The slurry was then filtered on a 1-micron polypropylene cloth to obtain a concentrated liquid weighing 270 g. and a black filter cake weighing 108.4 g.

The liquid concentrate was divided into two equal portions to which were added an equal weight of either a polyester lubricant or a hydro-treated naphthenic oil. The product had an absorbance at 528 nm (hexane) and an emission maximum at 539 nm. The liquid products were stable when stored at –20° C.

EXAMPLE 2

The same reaction procedure was used as in Example 1 except 56.0 grams (0.10 g—mol) of C.I. Vat Blue 18 and only 400 grams lauryl chloride were charged to the flask. The reaction proceeded the same except for the final heating cycle which lasted 15.5 hours at 221° C. The temperature was then lowered to 80° C.

This reaction slurry was filtered at 80° C. on a 1 micron polypropylene cloth to obtain 215 g, liquid concentrate and a filter cake of 104.6 g.

The concentrate was divided into four equal portions by weight. To each portion was added an equal weight of either a hydro-treated napthenic oil, a polyalkyleneglycol, a polyol ester solvent or an alkyl benzene solvent. All four solutions showed good storage stability after one month at –20° C.

The liquid product had a maximum absorbance at 501 nm (hexane) and maximum emission peak at 510 nm.

EXAMPLES 3–5

Additional dyes were prepared having the characteristics set forth in the table below:

| Example | Vat Starting Dye | Color of Fluorescence | Long Wavelength Absorption, nm | Emission Wavelength nm |
|---|---|---|---|---|
| 3 | Violet 9 | Green-Yellow | 524 | 531 |
| 4 | Black 16 | Yellow-Green | 494 | 509 |
| 5 | Green 1 | Yellow | 498 | 534. |

What is claimed is:

1. Fluorescent dye having the formulae:

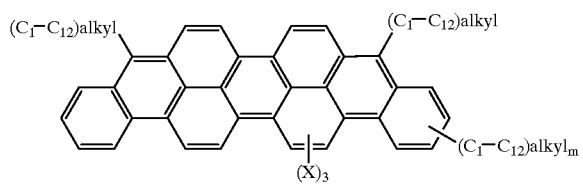

(I_f)

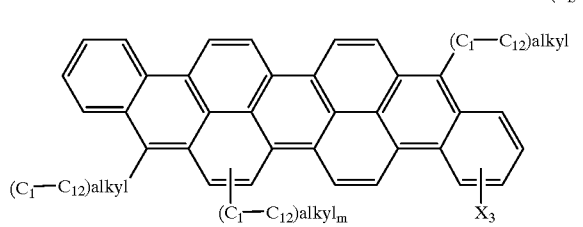

(II_f)

where the Xs are the same or different and are selected from H, Cl, F, I, O—(C1–C8)alkyl, and NY$_2$ where the Ys are the same or different and are selected from H or (C1–C1)alkyl; provided that at least one X is other than H and m=1–4.

2. A method of synthesizing the dyes of claim 1 comprising providing dye of the formula:

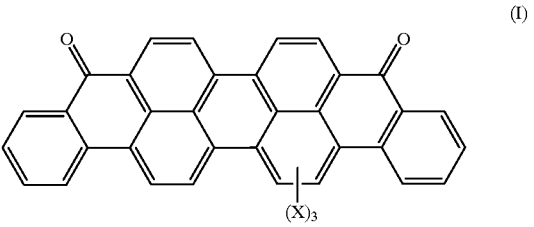

(I)

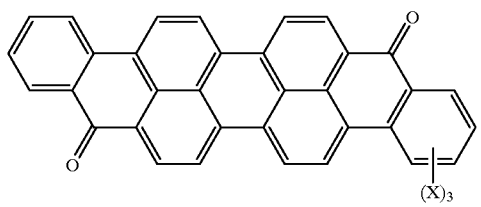
(II)
where the Xs are the same or different and are selected from H, Cl, F, I, O—(C1–C8)alkyl, and $NY_2$ where the Ys are the same or different and are selected from H or (C1–C8)alkyl; provided that at least one X is other than H,
and reacting said dye of formulae (I) or (II) with an excess of alkyl halide in the presence of zero valence zinc.
* * * * *